US009428769B2

(12) United States Patent
Ramanujan et al.

(10) Patent No.: US 9,428,769 B2
(45) Date of Patent: Aug. 30, 2016

(54) LIPOSOME, PROTEOLIPOSOME, BIOCHIP, AND METHOD FOR PRODUCING LIPOSOME AND PROTEOLIPOSOME

(75) Inventors: Chandra Sekar Ramanujan, Oxford (GB); Nahoko Kasai, Atsugi (JP); Keiichi Torimitsu, Atsugi (JP); John F. Ryan, Oxford (GB)

(73) Assignees: Nippon Telegraph and Telephone Corporation, Tokyo (JP); Isis Innovation Ltd., Oxford (GB)

( * ) Notice: Subject to any disclaimer, the term of this patent is extended or adjusted under 35 U.S.C. 154(b) by 1967 days.

(21) Appl. No.: 12/324,035

(22) Filed: Nov. 26, 2008

(65) Prior Publication Data

US 2010/0130382 A1 May 27, 2010

(51) Int. Cl.
| | | |
|---|---|---|
| C40B 40/14 | (2006.01) | |
| C12N 15/88 | (2006.01) | |
| A61K 9/127 | (2006.01) | |

(52) U.S. Cl.
CPC .............. *C12N 15/88* (2013.01); *A61K 9/1272* (2013.01); *B01J 2219/0074* (2013.01); *B01J 2219/00527* (2013.01); *B01J 2219/00659* (2013.01); *B01J 2219/00734* (2013.01); *Y10T 428/2984* (2015.01)

(58) Field of Classification Search
None
See application file for complete search history.

(56) References Cited

U.S. PATENT DOCUMENTS

2008/0319169 A1* 12/2008 Firestone et al. ............. 530/350
2010/0034807 A1* 2/2010 Moyle ........................ 424/130.1

OTHER PUBLICATIONS

Gandhavadi et al (2002 Biophysical Journal 82:1469-1482).*
Laroche et al (2005 Biochimica et Biophysica Acta 1669:8-16).*
Chen et al (2001 Biophysical Journal 80:254-70).*
Almeida, Rodrigo F. M. de, et al., "Lipid Rafts have Different Sizes Depending on Membrane Composition: A Time-resolved Fluorescence Resonance Energy Transfer Study," Journal of Molecular Biology, 346, pp. 1109-1120 (2005), Elsevier Ltd.
Weerachatyanukul, Wattana, et al., "Visualizing the localization of sulfoglycolipids in lipid raft domains in model membranes and sperm membrane extracts," Biochimica et Biophysica Acta, 1768, pp. 299-310 (2007), Elsevier B.V.
Lichtenberg, Dov, et al., "Phase boundaries in mixtures of membrane-forming amphiphiles and micelle-forming amphiphiles," Biochimica et Biophysica Acta, 1508, pp. 1-19 (2000), Elsevier Science B.V.
Brockmann, Rainer A., et al., "Spontaneous Formation of Detergent Micelles around the Outer Membrane Protein OmpX," Biophysical Journal, vol. 88, pp. 3191-3204 (May 2005), Biophysical Society.
Vaithianathan, Thirumalini, et al., "Neural Cell Adhesion Molecule-associated Polysialic Acid Potentiates a-Amino-3-hydroxy-5-methylisoxazole-4-propionic Acid Receptor Currents," The Journal of Biological Chemistry, vol. 279, No. 46, pp. 47975-47984 (Nov. 12, 2004), The American Society for Biochemistry and Molecular Biology, Inc.

* cited by examiner

*Primary Examiner* — Karen S Weiler
(74) *Attorney, Agent, or Firm* — Harness, Dickey & Pierce, P.L.C.

(57) ABSTRACT

A liposome comprising a region of a lipid bilayer membrane with different membrane thicknesses, wherein each lipid bilayer membrane region is composed of a different lipid, and a thick membrane side in the region of the lipid bilayer membrane is formed of lipid having a phase transition temperature higher than that of the lipid forming a thin membrane side in the region of the lipid bilayer membrane. A proteoliposome, wherein the above-described liposome includes membrane proteins. A biochip, wherein the above-described liposome or the above-described proteoliposome is spread on a substrate. The above-described biochip, wherein the substrate includes at least one kind selected from the group consisting of mica, $SiO_2$, SiN, Au and Pt.

10 Claims, 3 Drawing Sheets

LIPOSOME, PROTEOLIPOSOME, BIOCHIP, AND METHOD FOR PRODUCING LIPOSOME AND PROTEOLIPOSOME

BACKGROUND OF THE INVENTION

1. Field of the Invention

The present invention relates to a liposome, a proteoliposome, a biochip, and a method for producing the liposome and the proteoliposome.

2. Description of the Related Art

In natural cell membranes, there exist microdomains (lipid rafts) composed of mixed lipid including phospholipids of different chain lengths and molecules other than phospholipids, such as cholesterol. The lipid rafts are considered to be the center for inserting receptor proteins and seem to play a key role in signal transduction. More specifically, the lipid rafts are considered to have a function of organizing or separating neurotransmitter receptors so as to increase or decrease the signal transduction in central nervous system synapses.

The structure of the lipid raft in a cell membrane is not static, but rather shows a change in physiological state. Concretely, the lipid rafts of the synaptic membrane change by stimulation due to bleeding or food intake. Furthermore, organization of receptor proteins of the lipid rafts immediately shows a change according to an ambient environment of the lipid bilayer membrane (hereinafter, also may be referred to as a "lipid membrane"), and this is believed to be so because the change in a lipid raft structure has an effect on the density of receptor proteins in the lipid raft.

As mentioned above, since the lipid rafts play an important role in signal transduction, the structure and function have been examined extensively by forming a natural lipid raft-like lipid structure (hereinafter, referred to as a "raft-like structure"). The raft-like structure is formed by including molecules other than lipid, such as cholesterol (for example, see Rodrigo F. M. de Almeida, Luis M. S. Loura, Alexander Fedorov and Manuel Prieto, J. Mol. Biol., 346, 1109-1120 (2005) and Wattana Weerachatyanukul, Ira Probodh, Kessiri Kongmanas, Nongnuj Tanphaichitr, Linda J. Johnston, Biochimica et Biophysica Acta, 1768, 299-310 (2007)).

However, for the methods described in Rodrigo F. M. de Almeida, Luis M. S. Loura, Alexander Fedorov and Manuel Prieto, J. Mol. Biol., 346, 1109-1120 (2005) and Wattana Weerachatyanukul, Ira Probodh, Kessiri Kongmanas, Nongnuj Tanphaichitr, Linda J. Johnston, Biochimica et Biophysica Acta, 1768, 299-310 (2007), the temperature upon mixing had to be high to some extent so as to sufficiently mix molecules other than lipid, like cholesterol, with lipid, and thus the operation became complicated. In addition, in the case of a high molecular weight molecule such as cholesterol, it has been particularly difficult to reconstitute membrane proteins in the raft-like structure, thereby making it difficult to prepare a specimen having membrane proteins. Moreover, the production cost became expensive due to the use of molecules other than lipid.

Therefore, a method for easily forming a raft-like structure without using molecules other than lipid, such as cholesterol is required.

SUMMARY OF THE INVENTION

An object of the invention is to provide a liposome and a proteoliposome which have raft-like structures formed without employing molecules other than lipid, such as cholesterol, and a biochip which is manufactured by using them.

Another object of the invention is to provide a method for easily producing a liposome and a proteoliposome which have raft-like structures without using molecules other than lipid, such as cholesterol.

A liposome according to an aspect of the invention has a region of a lipid bilayer membrane with different membrane thicknesses, the liposome being characterized in that each lipid bilayer membrane region is composed of a different lipid, and a thick membrane side in the region of the lipid bilayer membrane is formed of a lipid having a transition temperature higher than that of a lipid forming a thin membrane side in the region of the lipid bilayer membrane.

A proteoliposome according to an aspect of the invention has membrane proteins in the liposome.

In a biochip according to an aspect of the invention, the liposome or the proteoliposome is spread on a substrate.

In the biochip according to an aspect of the invention, the substrate preferably includes at least one kind selected from the group consisting of mica, $SiO_2$, SiN, Au and Pt.

A production method for liposome according to an aspect of the invention is a method for producing a liposome including a region of a lipid bilayer membrane with different membrane thicknesses, the method including: a mixing step to obtain a mixed solution by mixing two or more kinds of lipids whose phase transition temperatures are different, and a surfactant; a temperature adjusting step to adjust the temperature of the mixed solution to be between the highest phase transition temperature and the lowest phase transition temperature of the lipid; and a membrane forming step to form a lipid bilayer membrane by removing the surfactant from the mixed solution.

A production method for proteoliposome according to an aspect of the invention is a method for producing a proteoliposome including a region of a lipid bilayer membrane with different membrane thicknesses, the method including: a mixing step to obtain a mixed solution by mixing two or more kinds of lipids whose phase transition temperatures are different, a surfactant and membrane proteins; a temperature adjusting step to adjust a temperature of the mixed solution to be between the highest phase transition temperature and the lowest phase transition temperature of the lipid; and a membrane forming step to form a lipid bilayer membrane by removing the surfactant from the mixed solution.

The liposome and proteoliposome of aspects of the invention have raft-like structures formed without employing molecules other than lipid, such as cholesterol. In addition, the biochip according to the aspect of the invention has a lipid bilayer membrane which has a raft-like structure formed without employing molecules other than lipid, such as cholesterol.

According to the production method of the aspect of the invention, liposome and proteoliposome which have raft-like structures formed without employing molecules other than lipid, such as cholesterol, can be easily produced.

DETAILED DESCRIPTION OF THE INVENTION

Figure 1A:
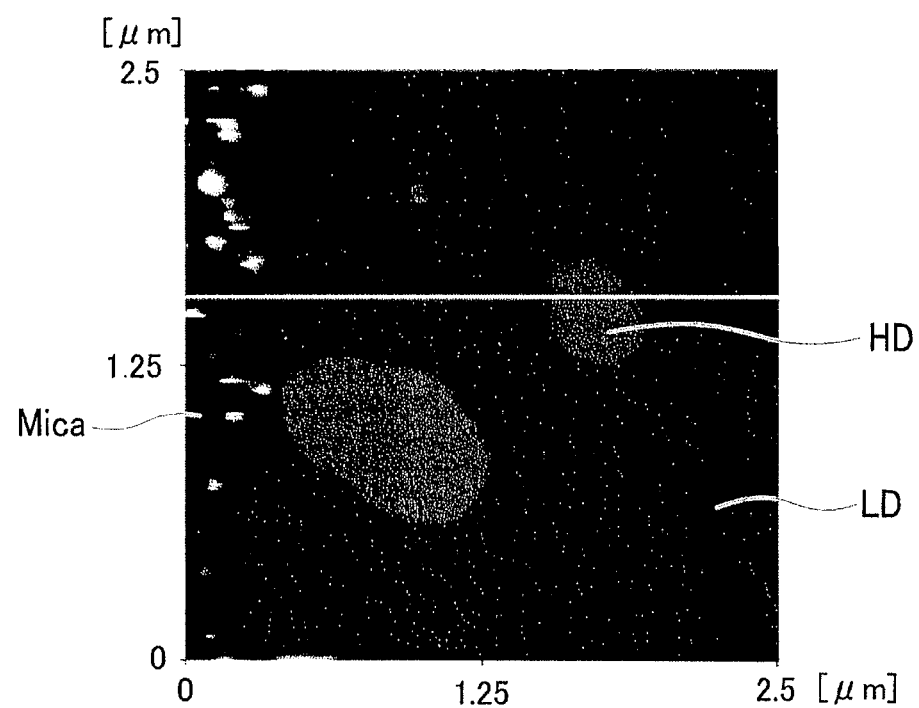
FIG. 1A is a figure showing an AFM image in Example 1.

While preferred embodiments of the invention will be described and illustrated below, it should be understood that these are exemplary of the invention and are not to be considered as limiting. Additions, omissions, substitutions, and other modifications can be made without departing from the spirit or scope of the present invention. Accordingly, the invention is not to be considered as being limited by the description, and is only limited by the scope of the appended claims.

Liposome

The liposome of the invention has a region of a lipid bilayer membrane with different membrane thicknesses, and each lipid bilayer membrane region is formed of different lipids. A thick membrane side in the region of the lipid bilayer membrane (hereinafter, referred to as an "H region") is formed of a lipid having a transition temperature higher than that of a thin membrane side in the region of the lipid bilayer membrane (hereinafter, referred to as an "L region").

For the lipid to be used in the invention, lipid having a phase transition temperature is adequate, and examples thereof may include egg phosphatidylcholine, egg phosphatidylglycerol, hydrogenated soy phosphatidylcholine (HSPC), distearoylphosphatidylcholine, distearoylphosphatidylglycerol, phosphatidylcholine (PC), phosphatidylglycerol (PG), lecithin, beta, glycolipid, γ-dipalmitoyl-α-lecithin, sphingomyelin (SPM), phosphatidylserine (PS), phosphatidic acid, N-(2,3-di(9-(Z)-octadecenyloxy))-prop-1-yl-N,N,N-trimethylammonium chloride, phosphatidylethanolamine (PE), lysolecithin, lysophosphatidylethanolamine, phosphatidylinositol (PI), cephalin, cardiolipin, cerebroside, dicetyl phosphate, dioleoyl phosphatidylcholine (DOPC), dipalmitoyl phosphatidylcholine, dipalmitoyl phosphatidylglycerol, dioleoyl phosphatidylglycerol, palmitoyl-oleoyl-phosphatidylcholine, distearoylphosphatidylcholine (DSPC), dimyristoylphosphatidylcholine (DMPC), dimyristoylphosphatidylglycerol, (DMPG), stearoyl-palmitoyl-phosphatidylcholine, di-palmitoyl-phosphatidylethanolamine, di-stearoyl-phosphatidylethanolamine, di-myristoyl-phosphatidylserine (DMPS), di-oleoyl-phosphatidylcholine, di-oleoyl-palmitoyl-phosphatidylcholine, monosialoganglioside, dilinoleoylphosphatidylcholine and the like.

For the lipid of the invention, two or more kinds among the above, whose phase transition temperatures are different, are used in combination.

The liposome of the invention is used at a temperature between the phase transition temperature of lipid forming an H region (hereinafter, referred to as "$T_H$") and the phase transition temperature of lipid forming an L region (hereinafter, referred to as "$T_L$"). The lipid becomes a gel phase to form an H region having a thick membrane when the $T_H$ is higher than the operating temperature, and the lipid becomes a liquid crystal phase to form an L region having a thin membrane when the $T_L$ is lower than the operating temperature. The operating temperature for the invention is its operating temperature when the liposome of the invention is used for Drug Delivery System (DDS) or the like, and its measured temperature when the liposome is observed through an optical microscope or measured by a drug screening or the like.

In the liposome of the invention, the membrane thickness of the H region is approximately 7 nm and the membrane thickness of the L region is approximately 5 nm.

Furthermore, for the lipid to be used, those having different acyl chain lengths may be used in combination, or those having bent molecules which have unsaturated bonds may be used in combination. These differences of the structure in the lipid to be used have little influence on the membrane thickness as compared with the difference of the phase transition temperature.

Moreover, the lipid to be used in the invention is not particularly limited as long as it is two or more kinds of lipids with different phase transition temperatures. However, in the case where a liposome is used in a living body, lipid whose $T_H$ is higher than an in vivo temperature (35 to 37° C.) and lipid whose $T_L$ is lower than the in vivo temperature are used. As a result, an H region is formed of the lipid having a high phase transition temperature and an L region is formed of the lipid having a low phase transition temperature, in the in vivo temperature to be used.

The lipid to be used may be three or more kinds. More specifically, in the case where a liposome in which four kinds of lipids having different phase transition temperatures are used, lipids whose $T_H$s are higher than the operating temperature form an H region, and lipids whose $T_L$s are lower than the operating temperature form an L region among the lipids. Concretely, for example, in the case where four kinds of lipids whose phase transition temperatures are 50, 40, 20 and 10° C. are used, two kinds of lipids whose phase transition temperatures are 50 and 40° C. form an H region and lipids whose phase transition temperatures are 20 and 10° C. form an L region when the operation temperature is 30° C. In the case where the same four kinds of lipids are used, when the operating temperature is 15° C., three kinds of lipids whose phase transition temperatures are 50, 40 and 20° C. form an H region and lipid whose phase transition temperature is 10° C. forms an L region.

In the liposome of the invention, the ratio of the H region in the lipid bilayer membrane can be increased by increasing the ratio of lipid which forms the H region.

The liposome of the invention may be filled with components such as drugs in the lipid membrane or the inner cavity, if needed.

Moreover, a labeling reagent such as a fluorescent reagent may be filled into the inner cavity. By filling a different labeling reagent in each liposome having different membrane proteins, they can be easily identified. Examples of the labeling reagent may include FITC (registered trademark, fluorescein), rhodamine, Cy3 (registered trademark), Cy5 (registered trademark) and the like.

Method for Producing Liposome

Hereinafter, one example of a method for producing a liposome will be illustrated.

A liposome of the invention can be obtained by a production method including: a mixing step to obtain a mixed solution by mixing two or more kinds of lipids whose phase transition temperatures are different, and a surfactant; a temperature adjusting step to adjust a temperature of the mixed solution to be between the highest phase transition temperature and the lowest phase transition temperature of the lipid; and a membrane forming step to form a lipid bilayer membrane by removing the surfactant from the mixed solution.

The mixed solution is obtained by mixing the lipid and the surfactant in the mixing step. Examples of the medium of the mixed solution may include aqueous media such as water, brine and a buffer solution. Examples of the buffer solution may include lactic acid, phosphoric acid, citric acid, boric acid, trishydroxymethylaminomethane, 2-(4-(2-hydroxyethyl)-1-piperazinyl)ethane sulfonic acid (HEPES) and the like.

Nonionic surfactants, anionic surfactants, cationic surfactants and zwitterionic surfactants can be used as a surfactant.

The nonionic surfactant may include D-octyl-n-glucoside, polyoxyethylene alkyl ether (AE), polyoxyethylene alkylphenol ether, alkyl glucoside (AG), polyoxyethylene fatty acid ester, sucrose fatty acid ester, sorbitan fatty acid ester, polyoxyethylene sorbitan fatty acid ester, fatty acid alkanolamide, diethanolamide, Tween, Triton and the like.

Examples of the anionic surfactant may include cholate, deoxycholate, glycolate, fatty acid sodium salt, monoalkyl sulfate, alkyl polyoxyethylene sulfate, alkyl benzene sulfonate, monoalkyl phosphate and the like.

Examples of the cationic surfactant may include alkyl trimethylammonium salt, dialkyl dimethylammonium salt, alkyl benzyl dimethyl ammonium salt, cetyltrimethylammonium bromide (CTAB) and the like.

Examples of the zwitterionic surfactant may include 3-(dodecyldimethyl-ammonio)propanesulfonate, polyoxyethylene alkyl ether, sorbitan fatty acid ester, fatty acid diethanolamide alkylmonoglyceryl ether, 3-((3-cholamidopropyl)dimethylammonio)-1-propanesulfonate (CHAPS), myristyl sulfobetaine (SB3-14) and the like.

These surfactants may be used only singly or in combination of two or more kinds thereof.

A content of lipid in the mixed solution is preferably 1.0 to 5.0 mM, more preferably 2.0 to 3.0 mM.

A content of the surfactant in the mixed solution to be used for preparing a liposome is preferably the amount equal to or more than the maximum amount $W_A$ of a surfactant associating with the lipid. When the content of the surfactant is $W_A$ or more, a sufficient amount of the surfactant associates with lipid and membrane proteins become stable in the mixed solution, and as a result, aggregation of membrane proteins can be suppressed in the mixed solution. Besides, the upper limit of the surfactant content may be an amount soluble in an aqueous solvent since adverse effects are small even if a large amount of surfactant is used.

The maximum amount $W_A$ of the surfactant is 3 mol per 1 mol of lipid molecules when octylglucoside is used, according to Lichtenberg, et al., Biochimica et Biophysica Acta, 1508, 1-19 (2000).

The mixed solution can be prepared by adding lipid and a surfactant to an aqueous medium to dissolve by stirring. Moreover, when drugs or the like are filled in a liposome, those components may be added in the mixed solution.

In the temperature adjusting step, the temperature of the mixed solution is adjusted to be between the highest phase transition temperature and the lowest phase transition temperature of the lipid.

By adjusting a liposome between the highest phase transition temperature and the lowest phase transition temperature to an operating temperature, an H region is formed of lipids whose phase transition temperature is higher than the temperature and an L region is formed of lipids whose phase transition temperature is lower than the temperature in the temperature adjusting step.

In the membrane forming step, a lipid bilayer membrane is formed by removing a surfactant from the mixed solution, thereby obtaining a liposome.

The surfactant can be removed from the mixed solution by a known method, and examples thereof may include dialysis using a cellulosic semipermeable membrane or the like and a bead method using a hydrophobic adsorbent (beads).

The dialysis is preferably carried out at about 4° C. over a few days to a week.

By removing the surfactant in the mixed solution gradually by these methods, a liposome which is composed of a lipid bilayer membrane is formed from stabilized lipid in the mixed solution.

The particle diameter of the liposome can be made uniform by an ultrasonic agitation method. A sonicator to be used may be either a probe or bath type. However, the probe type has the possibility of metal ions being mixed in the mixed solution since a metal tip comes into contact with the mixed solution. In addition, it is difficult to obtain a liposome having excellent uniformity since the ultrasonic waves are unequal in the mixed solution. Therefore, the sonicator is preferably a bath type.

Each step in the production method of the invention is not limited to the above-mentioned order. More specifically, the mixing step and the temperature adjusting step may be carried out at the same time by adding lipid and a surfactant to a medium which is adjusted to be the operating temperature of the liposome between the highest phase transition temperature and the lowest phase transition temperature, to mix. After the mixing step, a membrane forming step is carried out by dialysis at 4° C., and then a temperature adjusting step which adjusts the temperature of the mixed solution to one between the highest phase transition temperature and the lowest phase transition temperature in the lipid may be carried out. After the mixing step, the temperature adjusting step and the membrane forming step may be carried out at the same time by removing the surfactant by dialysis, a bead method or the like in a state of adjusting the temperature of the mixed solution between the highest phase transition temperature and the lowest phase transition temperature.

For a liposome of the invention, since a raft-like structure having a simple constitution is formed by an easy method, the ratio of an H region having the raft-like structure can be easily controlled by changing the composition of lipid. Therefore, it is suitable for application such as analysis to examine the structure and function of natural lipid rafts in detail or DDS.

Proteoliposome

A proteoliposome of the invention has membrane proteins in the liposome. That is, membrane proteins are reconstituted in a lipid membrane of the liposome in a proteoliposome of the invention.

The membrane protein may be disposed in a lipid bilayer of a cell membrane in vivo, and examples thereof may include ionotropic receptors, G protein-coupled receptors and the like.

Examples of the ionotropic receptor may include TRP (Transient Receptor Potential) channels (Subunits are TRPV1, TRPV2, TRPV3, TRPV4, TRPV5, TRPV6, TRPV8, TRPA1, TRPC1, TRPC2, TRPC3, TRPC4, TRPC5, TRPC6, TRPC7, TRPM1, TRPM2, TRPM3, TRPM4, TRPM5, TRPM6, TRPM7, TRPM8, TRPN1, TRPML1, TRPML2, TRPML3, TRPY1, TRPP1, TRPP2, TRPP3, TRPP4 and TRPP5) involved in cellular signal transduction, temperature sensitivity, inflammation and pain; ATP receptors (Subunits are P2X1, P2X2, P2X3, P2X4, P2X5, P2X6 and P2X7) involved in cellular signal transduction and pain; serotonin receptors (Subunits are 5-HT1, 5-HT2, 5-HT4, 5-HT6 and 5-HT7) involved in cellular signal transduction and affectivity; NMDA receptors (Subunits are NR1, NR2A and NR2B) involved in cellular signal transduction and excitatory neurotransmission; AMPA receptors (Subunits are GluR1, GluR2, GluR3 and GluR4) involved in cellular signal transduction and excitatory neurotransmission; kainate receptors (Subunits are GluR5 and GluR7) involved in cellular signal transduction and excitatory neurotransmission; GABA receptors (Subunits are GABAA receptor and GABAC receptor) involved in cellular signal transduction and inhibitory neurotransmission; and the like.

Examples of the G protein-coupled receptor may include adenosine receptors (A1, A2A, A2B and A3) involved in cellular signal transduction; ATP receptors (P2Y1, P2Y2, P2Y4, P2Y6, P2Y11, P2Y12, P2Y13 and P2Y14) involved in cellular signal transduction; serotonin receptors (5-HT3) involved in cellular signal transduction; adrenergic receptors ($\alpha$1, $\alpha$2, $\beta$1 and $\beta$2) involved in cellular signal transduction and pain; metabotropic glutamate receptors (mGluR1, mGluR2, mGluR3, mGluR5, mGluR6, mGluR7 and mGluR8) involved in cellular signal transduction; GABA receptors involved in cellular signal transduction; opioid receptors ($\nu$ receptor, $\delta$ receptor and $\kappa$ receptor) involved in cellular signal transduction and pain; and the like.

These membrane proteins may be used only singly or in combination of two or more kinds thereof.

The membrane protein may be bonded to a fluorescent material by a genetic engineering technique. A proteoliposome having specific membrane proteins can be easily identified by binding to a fluorescent material.

As the fluorescent material, known materials usually used for binding with proteins can be used, and examples thereof may include fluorescent proteins such as GFP, CFP and YFP. By allowing a fluorescent material to bond to a position outside the lipid bilayer membrane of a membrane protein in a proteoliposome, as well as allowing a fluorescent material to bond to a substance binding to the membrane protein, a conformational change of the membrane protein due to such binding can be detected at a single molecular level according to FRET (Fluorescence Resonance Energy Transfer).

The membrane proteins are primarily reconstituted in an H region in the proteoliposome of the invention. This is considered to be because the lipid bilayer membrane of the H region is thicker than that of the L region so that the hydrophobic part is large and the hydrophobic interaction between the hydrophobic part and the transmembrane domain of the membrane protein is strong, as compared with the L region. It is possible to control the density of receptor proteins in the proteoliposome per unit area by varying the composition of the lipid mixture.

The proteoliposome of the invention may be filled with components such as drugs in the lipid membrane or the inner cavity, if needed.

Moreover, a labeling reagent such as a fluorescent reagent may be filled in the inner cavity. By filling a different labeling reagent into each proteoliposome having a different membrane protein, they can be easily identified. Examples of the labeling reagent may include FITC (registered trademark, fluorescein), rhodamine, Cy3 (registered trademark), Cy5 (registered trademark) and the like.

Method for Producing Proteoliposome

Hereinafter, an exemplary embodiment of the method for producing a proteoliposome of the invention will be illustrated.

The liposome of the invention can be obtained by a production method including: a mixing step to obtain a mixed solution by mixing two or more kinds of lipids whose phase transition temperatures are different, membrane proteins and a surfactant; a temperature adjusting step to adjust the temperature of the mixed solution to be between the highest phase transition temperature and the lowest phase transition temperature of the lipid; and a membrane forming step to form a lipid bilayer membrane by removing the surfactant from the mixed solution.

A content of lipid in the mixed solution is preferably 1.0 to 5.0 mM, more preferably 2.0 to 3.0 mM.

A content of the membrane protein in the mixed solution differs depending on the kind of the membrane protein, but it is preferably $1 \times 10^{-5}$ to $1 \times 10^{-4}$ mol per mol of lipid, more preferably $3.3 \times 10^{-5}$ to $7.5 \times 10^{-5}$ mol.

The content of the surfactant in the mixed solution which is used for producing a proteoliposome is preferably 1.5 times of the total amount ($W_A+W_B$) of the maximum amount of a surfactant associating with the lipid $W_A$ and the maximum amount of a surfactant associating with the membrane protein $W_B$ or more, more preferably 2.0 times or more. In the case where the content of the surfactant is 1.5 times of the total amount ($W_A+W_B$) or more, a sufficient amount of the surfactant associates with lipid and membrane proteins to be stable in the mixed solution, and as a result, aggregation due to the membrane proteins coming in contact with each other can be easily suppressed in the mixed solution. In addition, since membrane proteins gradually move into the lipid membrane to be reconstituted, it is difficult for aggregation of membrane proteins to occur in the obtained proteoliposome. Accordingly, a proteoliposome in which the membrane proteins are reconstituted in a lipid membrane with aggregation of the membrane proteins suppressed can be easily obtained. The upper limit of the surfactant content may be an amount soluble in an aqueous solvent since adverse effects are small, even if there is an excess of surfactant.

The maximum amounts $W_A$ of the surfactant is in the same manner as $W_A$ of the surfactant in a liposome. An association number of the surfactant to transmembrane domain portions of membrane proteins, that is $W_B$, is considered in Bockman R. A. et al., Biophysical Journal, 61, 1176-1183 (2005). That is, when the length of a transmembrane portion is 2.5 nm and the diameter is 2.8 nm, the association number of the surfactant DHPC is 80 molecules. The association number ($W_B$) is estimated from the kinds of the surfactant or the size of the transmembrane portion.

For example, in the case where the lipid is mixed lipid (mass average molecular weight 800) in which PC (egg yolk) and PS (derived from swine brain) are mixed in the proportion of 3:1 and the surfactant is octyl glycoside (OG, molecular weight 292), the surfactant associating with 1 mol of the mixed lipid is 3 mol. In the case where the membrane protein is an AMPA receptor and the surfactant is OG, the surfactant associating with 1 mol of the AMPA receptor is 240 mol. Accordingly, in the case where the mixed lipid m mol and a membrane protein n mol are used, the amount of the surfactant is ($W_A+W_B$)=(3 m+240 n) mol or more.

The mixed solution can be prepared by adding lipid, membrane proteins and a surfactant to an aqueous medium to dissolve by stirring. Moreover, when encapsulating a drug or the like in a proteoliposome, those components may be added in the mixed solution.

A temperature when mixing the lipid, membrane proteins and surfactant is preferably 37° C. or less, though it differs depending on the kind of lipid and membrane protein.

The surfactant can be removed from the mixed solution by a known method, and examples thereof may include dialysis, a bead method, which were described in the method for producing a liposome, or the like.

The dialysis is preferably carried out at about 4° C. over a few days to a week.

By removing the surfactant in the mixed solution gradually by these methods, a liposome which is composed of a lipid bilayer membrane is formed from stabilized lipid in the mixed solution while stabilized membrane proteins in the mixed solution gradually move into the lipid bilayer membrane, and then are reconstituted to be stabilized.

The particle diameter of the proteoliposome can be made uniform by an ultrasonic agitation method. A sonicator to be used may be either a probe or bath type as in the production method for a liposome, but is preferably a bath type.

Each step in the method for producing a proteoliposome according to the invention is not limited to the above-mentioned order. More specifically, the mixing step and the temperature adjusting step may be carried out at the same time by adding lipid, membrane proteins and a surfactant to a medium which is adjusted to be the operating temperature of the liposome between the highest phase transition temperature and the lowest phase transition temperature, to mix. After the mixing step, a membrane forming step is carried out by dialysis or the like at 4° C., and then a temperature adjusting step which adjusts the temperature of the mixed solution to one between the highest phase transition temperature and the lowest phase transition temperature may be carried out. After the mixing step, the temperature adjusting step and the membrane forming step may be carried out at the same time by removing the surfactant by dialysis, a bead method or the like in a state of adjusting the temperature of the mixed solution between the highest phase transition temperature and the lowest phase transition temperature. It is possible to control the density of receptor proteins in the proteoliposome per unit area by varying the composition of the lipid mixture.

With regard to the proteoliposome of the invention, a raft-like structure having a simple constitution is formed by an easy method, and membrane proteins are primarily reconstituted in the H region. Therefore, the proteoliposome can be used in a state for observation through an electron microscope or the like in order to examine the structure and function of the lipid raft and membrane proteins. The proteoliposome can be used in the field of nanomedicine such as DDS by filling drugs or the like in the inner cavity.

Biochip

A biochip of the invention is one in which the above-mentioned liposome or proteoliposome of the invention is spread on a substrate.

A substrate of the invention may be used for a substrate of a biochip, and it is preferably a substrate including one or more kinds selected from the group consisting of glass, mica, $SiO_2$, SiN, Au and Pt.

A microstructure may be formed on the surface of the substrate in order to allow an easy spread of a lipid bilayer membrane.

Examples of the method of spreading the liposome or proteoliposome on a substrate may include a vesicle fusion method. The vesicle fusion method is a method of transferring a lipid bilayer membrane onto the substrate by the interaction between the lipid bilayer membrane of a vesicle and the substrate, by immersing the substrate in a solution containing a spherical endoplasmic reticulum called a vesicle (a liposome or proteoliposome of the invention). It may be a method of adding the solution dropwise onto the substrate.

In the case where the liposome or proteoliposome is spread on a substrate by this method, the substrate can be modified in order to improve the interaction between the surface of the substrate and the lipid bilayer membrane. Examples of the modification method for the surface of the substrate may include a method in which the surface of the substrate is modified with an amino group-containing substance to change it to a hydrophilic state, and the interaction between the substrate and the lipid bilayer membrane is improved by an electrostatic force.

Furthermore, a lipid bilayer membrane is formed on a substrate in advance, and the liposome or proteoliposome is spread on the lipid bilayer membrane. This leads to fusion of the lipid bilayer membrane on the substrate with the lipid bilayer membrane of the liposome or proteoliposome, and then membrane proteins are reconstituted to a lipid bilayer membrane on the substrate. Examples of the method of forming a lipid bilayer membrane on a substrate in advance may include a method in which the above-mentioned vesicle fusion method is carried out using a liposome not containing membrane proteins. The liposome in this case may be a liposome having no raft-like structure like the invention.

For the observation method of the membrane protein in a biochip, for example, AFM, scanning probe microscopy (SPM) other than AFM, total internal reflection fluorescence (TIFR), optical microscopy or the like can be used. Among them, AFM is preferably used in the case of observation of a single membrane-protein molecule.

Reconstituted membrane proteins in the lipid bilayer membrane are closer to the intravital state than membrane proteins remaining purified. For that reason, more reliable results can be obtained in a drug screening or biological use by using membrane proteins with the membrane proteins reconstituted in the lipid bilayer membrane like this.

Moreover, membrane proteins are mainly reconstituted in the H region of a lipid bilayer membrane which is formed on a substrate in the biochip of the invention. Therefore, by adjusting the composition of the lipid, a limited ratio of an H region is formed, and membrane proteins can be built up in the H region. It is considered that, for example, an interaction or the like between different membrane proteins can be examined by using two or more kinds of membrane proteins and building them up in the H region to reconstitute if this property is utilized.

The ratio of the H region of the lipid bilayer membrane in the biochip is not particularly limited, but the size of the H region is preferably 1 $\mu m^2$ or more. If the size of the H region is 1 $\mu m^2$ or more, aggregation of membrane proteins in the H region can be easily suppressed, observation, analysis or the like of the raft-like structure and membrane protein by fluorescence microscope can become easy. The size of the H region can be adjusted by regulating the amount of lipid having a high phase transition temperature to be used for producing a proteoliposome.

The interval of the membrane proteins in the H region of the lipid bilayer membrane of a biochip is preferably 50 to 100 nm. When the interval between the membrane proteins is 50 nm or more, it is easy to observe and analyze the membrane protein at a single molecular level. When the interval between the membrane proteins is 100 nm or less, sufficient number of membrane proteins can be easily reconstituted in the H region, and it becomes easy to observe or analyze the raft-like structure and membrane protein in the same state as in in vivo.

The membrane protein in the biochip of the invention is reconstituted to face the same direction. Specifically, it is energetically more stable for a transmembrane domain of the membrane protein to exist inside the lipid domain because of a hydrophobic interaction with an alkyl chain of a lipid molecule in the lipid membrane. Therefore, the membrane protein is reconstituted by locating the transmembrane domain inside the lipid membrane and the rest on the lipid membrane to face the same direction. Consequently, the structure and conformational change of the membrane protein can be examined by observing a single molecule without observing a number of membrane proteins and knowing the direction by analogy.

In addition, since the structure of the membrane protein is maintained by reconstitution, its function is also maintained. Therefore, membrane proteins in the raft-like structure can be directly examined effectively and efficiently by observing the membrane protein maintaining the activity. According to this, a performance of a drug target with respect to a specific membrane protein receptor dramatically improves. Consequently, it is expected to be widely used not only in drug screening in drug discovery but also in the field of diagnosis in which membrane proteins are detected.

Raft-like structures having a simple constitution are formed by an easy method in the liposome, proteoliposome and biochip of the invention described above. Since the raft-like structure is simpler as compared with a structure using the conventional molecules such as cholesterol, not only operation upon production but also reconstitution of membrane proteins to a lipid membrane is easy.

Furthermore, the liposome, proteoliposome and biochip of the invention are very effective in order to examine the functions of a lipid raft in vivo and a membrane protein in the lipid raft since membrane proteins is primarily reconstituted in the H region of a raft-like structure.

EXAMPLES

Hereinafter, the present invention will be illustrated in detail with reference to examples and a comparative example. However, the invention is not limited by the following description.

Observation by AFM

A mica substrate which is obtained in the present example was observed by an atomic force microscope (AFM, D3100, manufactured by Veeco) having an OMCL-TR800PSA-1 (manufactured by OLYMPUS CORPORATION) as a cantilever with the top of the mica substrate filled with a buffer solution B (30 mM HEPES, 260 mM KCl, 40 mM NaCl, and pH 7.4) at 18° C.

Lipid

Four kinds of phosphatidylcholines which were phospholipids composed of 59% of a synaptic membrane were used in this example. These phosphatidylcholines were 1,2-dipalmitoyl-sn-glycero-3-phosphocholine (16:0, phase transition temperature 41° C.), 1,2-distearoyl-sn-glycero-3-phosphocholine (18:0, phase transition temperature 55° C.), 1,2-dioleoyl-sn-glycero-3-phosphocholine (18:1, phase transition temperature −20° C.) and 1,2-dilinoleoyl-sn-glycero-3-phosphocholine (18:2, phase transition temperature −53° C.) (hereinbefore, all produced by Avanti Polar Lipids, Inc.), which were obtained from egg phosphatidylcholine, and dissolved in chloroform. However, as for values in parentheses, the former number represents the carbon number of an acyl chain of lipid and the latter number represents the number of unsaturated bonds in which an acyl chain of lipid has.

These lipids which were dissolved in chloroform evaporate chloroform through dry nitrogen, were hydrated by a buffer solution A (30 mM HEPES, 5 mM EDTA, 1 mM EGTA, 0.02% $NaN_3$ and pH 7.4), subjected to sonication for 10 minutes, and then the resultant product was preserved at −20° C. until it dissolved on ice upon use.

Production Example 1

Production of AMPA Receptor

An AMPA receptor (GluR3) was obtained by purifying High-Five cells (produced by Invitrogen Corporation) which were overexpressed, based on the method described in J. Biol. Chem., 279, 47975 (2004).

High-Five cells ($10^8$ cells) were homogenized by a Potter type homogenizer using a buffer solution for homogenization (containing a protease inhibitor, produced by Roche), and solubilized by an ultracentrifuge. Next, a solubilized fraction was purified with wheat germ agglutinins (WGA)-sepharose CL4B (produced by Vector Laboratories), subsequently purified with diethylaminoethyl-sepharose CL6B (produced by Amersham Bioscience), thereby obtaining 8.4 µg/ml and 12.8 µg/ml of two purified AMPA receptor solutions. The obtained AMPA receptors were confirmed by Western blotting using SDS-PAGE (electrophoresis) and silver staining, and an anti-GluR2/3 antibody derived from rabbit (produced by Chemicon) and an HRP-labeled anti-rabbit IgG antibody (Jackson Immuno Research Laboratories).

Example 1

With the use of, as lipid, mixed lipid of lipid (16:0), lipid (18:0) and lipid (18:1) in a ratio of 10:30:60, and, as a surfactant, n-octyl-D-glucopyranoside (produced by Sigma), a mixed solution was obtained by mixing them with a buffer solution A (at room temperature for 10 minutes) such that the mixed lipid was 2.5 mM and the surfactant was 40 mM. The mixed solution was left to stand at room temperature for 10 minutes, dialyzed at 4° C. over 4 days, and then the surfactant was gradually removed to prepare a liposome. A cellulosic membrane (molecular weight 14000, produced by Spectrum) was used for the semipermeable membrane. The buffer solution A was used as an external solution of dialysis.

Then, the obtained solution was subjected to sonication at room temperature for 10 minutes, the solution (5 µl) was added dropwise on a mica substrate (3 µm square), and then left to stand in a wet container for a few minutes to form a lipid membrane on the mica substrate. Thereafter, the mica substrate was washed twice with a buffer solution B, and a sufficient amount of the buffer solution B for observation was added on the mica substrate, followed by observation using AFM.

Examples 2 to 5

Observation was made using AFM in the same manner as in Example 1, except that the composition of mixed lipid to be used was changed as shown in Table 1.

Figure 1B:
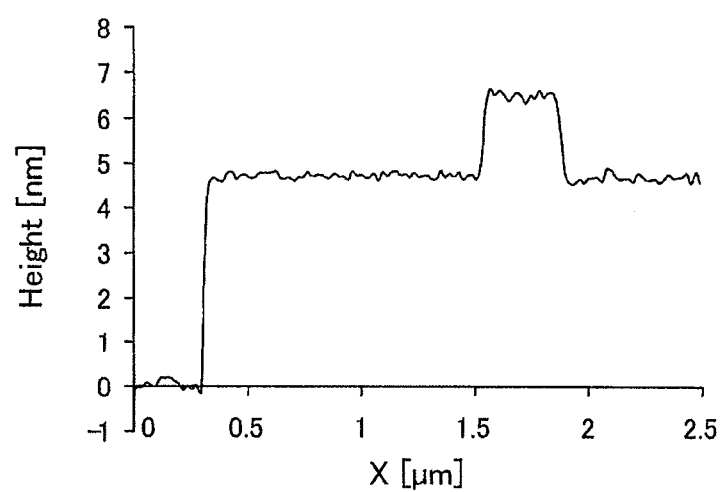
FIG. 1B is a figure showing a membrane thickness of a lipid membrane in Example 1.

Observations made by AFM in Example 1 are shown in FIG. 1A. In addition, the result in which the height from the mica substrate in the white line part was measured is shown in FIG. 1B. However, HD represents an H region, and LD represents an L region in FIG. 1A.

Figure 2:
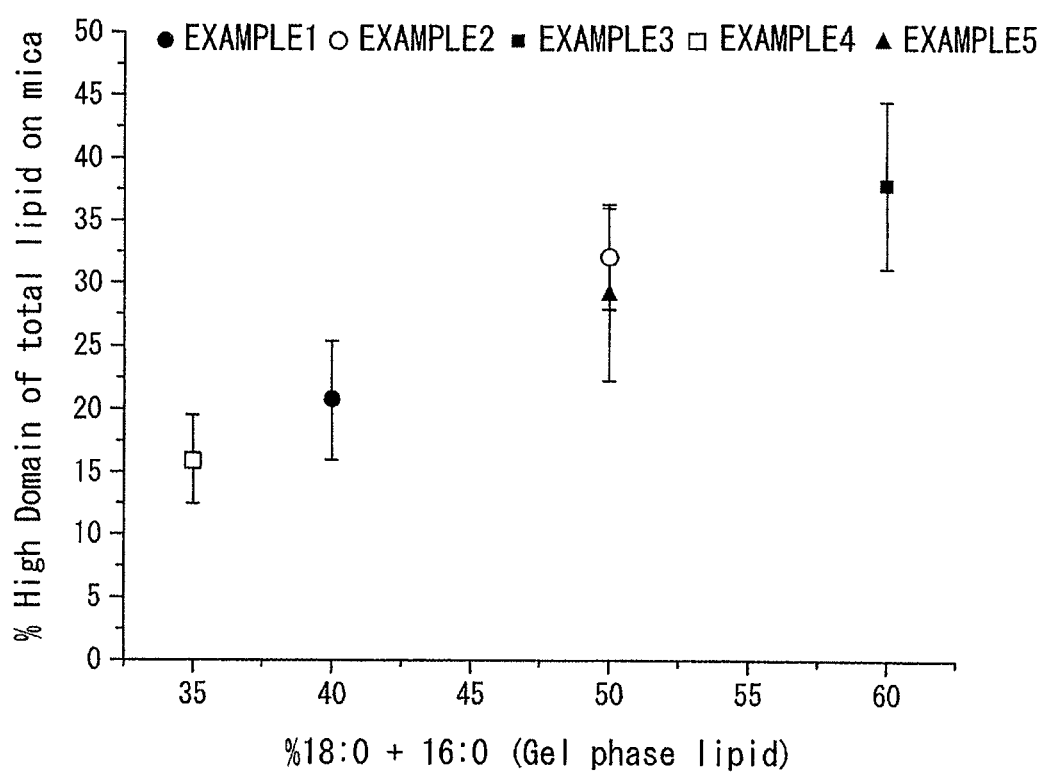
FIG. 2 is a figure showing the ratio of an H region in a lipid membrane on a mica substrate, to the ratio of lipid (16:0) and lipid (18:0) in Examples 1 to 5.

The relationship between the ratio of lipid (16:0) and lipid (18:0) in all the lipid (the ratio of lipid whose phase transition temperature is higher than the observational temperature) and the ratio of the formed H region in the lipid bilayer membranes on the mica substrates which were obtained in Examples 1 to 5, was shown in FIG. 2.

TABLE 1

| | Amount of Lipid [%] | | | |
|---|---|---|---|---|
| | 16:0 | 18:0 | 18:1 | 18:2 |
| Example 1 | 10 | 30 | 60 | 0 |
| Example 2 | 36 | 14 | 34 | 16 |
| Example 3 | 40 | 20 | 40 | 0 |
| Example 4 | 0 | 35 | 65 | 0 |
| Example 5 | 0 | 50 | 50 | 0 |

As shown in FIG. 1A and FIG. 1B, an H region was formed of lipid (16:0) and lipid (18:0) whose phase transition temperatures are higher than the observational temperatures of the AFM, and an L region was formed of lipid (18:1) whose phase transition temperature is lower than the observational temperature of the AFM, in Example 1 in which three kinds of lipids having different phase transition temperatures were used. Each membrane thickness of the H region and the L region was measured using a plurality of samples in which lipid bilayer membranes were formed on mica substrates under the same conditions, and the membrane thickness of the H region was 7.1±0.1 nm and the membrane thickness of the L region was 5.3±0.1 nm.

The same results as Example 1 were obtained with regard to Examples 2 to 5 as well.

Further, as shown in FIG. 2, it was confirmed that the ratio of the H region of the lipid bilayer membrane which was formed on the substrate was increased by increasing the ratio of lipid (16:0) and lipid (18:0) whose phase transition temperatures were higher than the observational temperatures, and the ratio of the H region in the formed lipid bilayer membrane could be controlled by changing the composition of the lipid.

Example 6

With the use of, as lipid, mixed lipid of lipid (18:0) and lipid (18:1) in a ration of 50:50, as a protein membrane, an AMPA receptor (GluR3) which was obtained in Production Example 1, and, as a surfactant, n-octyl-D-glucopyranoside (produced by Sigma), a mixed solution was obtained by mixing them with a buffer solution A (at room temperature for 10 minutes) such that the mixed lipid was 2.5 mM, the protein membrane was 120 nM, and the surfactant was 40 mM. The mixed solution was left to stand at room temperature for 10 minutes, dialyzed at 4° C. over 4 days, and then the surfactant was gradually removed to prepare a proteoliposome. A cellulosic membrane (molecular weight 14000, produced by Spectrum) was used for the semipermeable membrane. The buffer solution A was used as an external solution of dialysis.

Then, the obtained solution was subjected to sonication at room temperature for 10 minutes, the solution (5 µl) was added dropwise on a mica substrate (3 µm square), and then left to stand in a wet container for a few minutes to form a lipid membrane on the mica substrate. Thereafter, the mica substrate was washed twice with a buffer solution B, and a sufficient amount of the buffer solution B for observation was slowly added on the mica substrate, followed by observation using AFM.

Examples 7 and 8

Observation was made using AFM in the same manner as in Example 6, except that the composition of lipid was changed to the same as Examples 1 and 2.

Figure 3A:
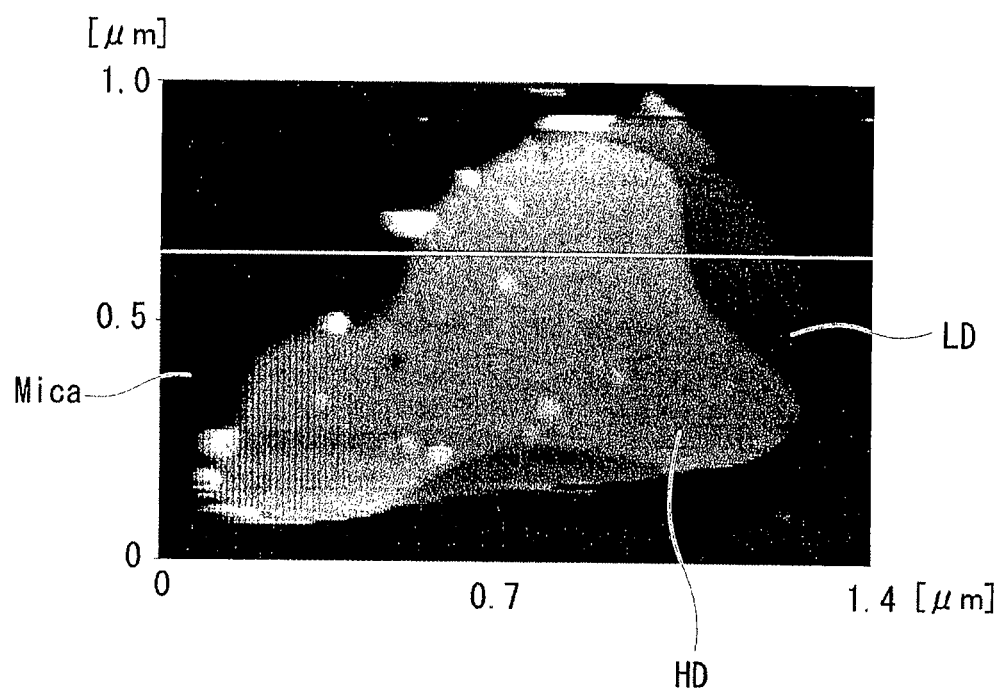
FIG. 3A is a figure showing an AFM image in Example 6.
Figure 3B:
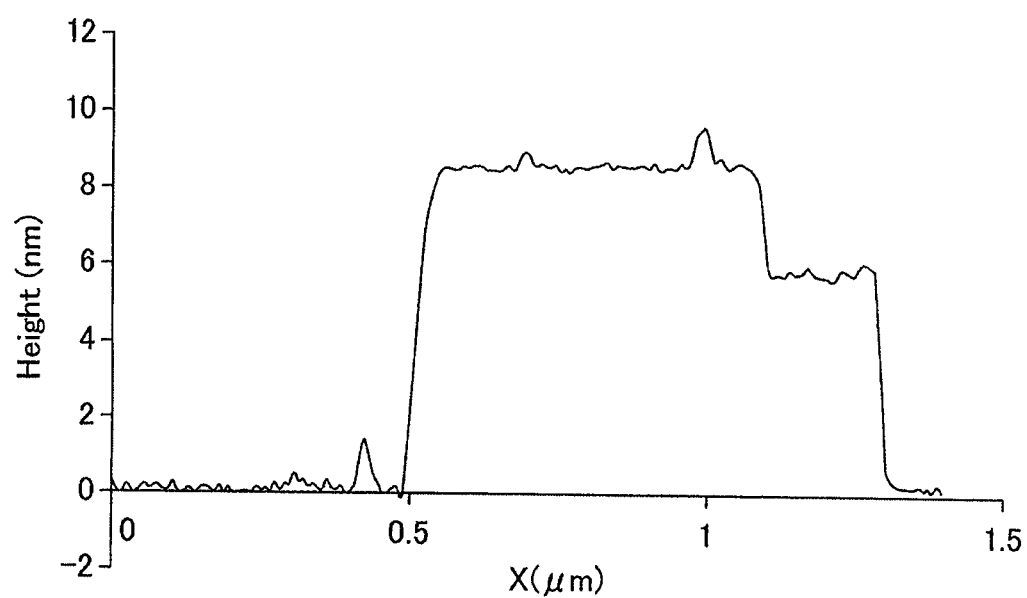
FIG. 3B is a figure showing a membrane thickness of a lipid membrane in Example 6.

Observations made by AFM in Example 6 are shown in FIG. 3A. In addition, the result in which the height from the mica substrate in the white line part in FIG. 3A was measured is shown in FIG. 3B. However, HD represents an H region, and LD represents an L region in FIG. 3A.

For Example 6, the number of membrane proteins which exist in the H region and the L region respectively, in the lipid bilayer membrane per 150,000 $nm^2$ on the mica substrate was counted, and the ratio of the number of membrane proteins in the L region based on the number of membrane proteins in the H region is shown in Table 2. In addition, the ratio of volume of membrane protein appearing above the lipid bilayer membrane in the L region based on the volume of membrane protein appearing above the lipid bilayer membrane in the H region is similarly shown in Table 2.

TABLE 2

| Normalized Number of Protein in a $1.5 \times 10^5$ $nm^2$ Area | | Normalized Volume of the Protein above Lipid Surface | |
|---|---|---|---|
| HD | LD | HD | LD |
| 1.0 | 0.35 | 1.0 | 1.4 |

As shown in FIG. 3A and FIG. 3B, membrane proteins are mainly reconstituted in a lipid bilayer membrane of the H region. Moreover, as shown in Table 2, it was confirmed that membrane proteins were mainly reconstituted in a lipid bilayer membrane in the H region since the number of membrane protein in the L region was 0.35 when the number of membrane proteins in the H region was 1.0.

The same results were obtained in Examples 7 and 8 (not shown in the figures).

When the volume of membrane protein appearing above a lipid bilayer membrane in the H region was 1.0, the volume of membrane protein appearing above a lipid bilayer membrane in the L region was 1.4. The volume of membrane protein appearing outside of a lipid bilayer membrane in the L region is larger in spite of the fact that the number of membrane proteins in the L region is fewer than that of membrane protein in the H region. This means that the membrane protein in the H region protrudes further outside the lipid bilayer membrane than the membrane protein in the L region.

From this result, it is considered that as for the hydrophobic interaction between the transmembrane domain of the membrane proteins and hydrophobic part of lipid bilayer membrane, the H region is stronger than the L region, and this causes membrane proteins to reconstitute preferentially in the H region.

A liposome, proteoliposome and biochip of the invention can form a simpler raft-like structure, and can be suitably used for examination or the like of a lipid raft and membrane proteins in the lipid raft. Accordingly, they can be suitably used in a wide range of fields such as medicine, pharmacy, diagnosis or the like.

What is claimed is:

1. A method for producing a liposome having a region of a lipid bilayer membrane with different membrane thicknesses comprising:
   a mixing step to obtain a mixed solution by mixing two or more kinds of lipids whose phase transition temperatures are different, and a surfactant;
   a temperature adjusting step to adjust the temperature of the mixed solution to be between the highest phase transition temperature among phase transition temperatures of the lipids and the lowest phase transition temperature among phase transition temperatures of the lipids;

a membrane forming step to form a lipid bilayer membrane by removing the surfactant from the mixed solution after the temperature adjusting step; and an ultrasonic agitating step to agitate the lipid bilayer membrane by exposing the lipid bilayer membrane to an ultrasonic wave, wherein the lipids are free of cholesterol.

2. A method for producing a proteoliposome having a region of a lipid bilayer membrane with different membrane thicknesses comprising:

a mixing step to obtain a mixed solution by mixing two or more kinds of lipids whose phase transition temperatures are different, a surfactant and a membrane protein;

a temperature adjusting step to adjust the temperature of the mixed solution to be between the highest phase transition temperature among phase transition temperatures of the lipids and the lowest phase transition temperature among phase transition temperatures of the lipids;

a membrane forming step to form a lipid bilayer membrane by removing the surfactant from the mixed solution after the temperature adjusting step; and an ultrasonic agitating step to agitate the lipid bilayer membrane by exposing the lipid bilayer membrane to an ultrasonic wave, wherein the lipids are free of cholesterol.

3. A method for producing a liposome having a region of a lipid bilayer membrane with different membrane thickness according to claim 1, wherein the highest phase transition temperature is higher than 37° C.; and the lowest phase transition temperature is lower than 35° C.

4. A method for producing a proteoliposome having a region of a lipid bilayer membrane with different membrane thickness according to claim 2, wherein the highest phase transition temperature is higher than 37° C.; and the lowest phase transition temperature is lower than 35° C.

5. A method for producing a proteoliposome having a region of a lipid bilayer membrane with different membrane thickness according to claim 2 or 4, wherein the membrane protein is an ionotropic receptor.

6. A method for producing a proteoliposome having a region of a lipid bilayer membrane with different membrane thickness according to claim 2 or 4, wherein the membrane protein is a G protein-coupled receptor.

7. The method for producing a liposome according to claim 1 or 3, wherein a labeling agent is included in the mixed solution in the mixing step, and the labeling agent is filled into an inner cavity of the liposome.

8. The method for producing a proteoliposome according to claim 2 or 4, wherein a labeling agent is included in the mixed solution in the mixing step, and the labeling agent is filled into an inner cavity of the proteoliposome.

9. The method for producing a liposome according to claim 1 or 3, wherein the region of a lipid bilayer membrane with different membrane thickness includes: a portion of a lipid bilayer with a layer thickness of approximately 7 nm; and a portion of a lipid bilayer with a layer thickness of approximately 5 nm, the portion of a lipid bilayer with a layer thickness of approximately 7 nm is made of a lipid with the highest transition temperature among the lipids, and the portion of a lipid bilayer with a layer thickness of approximately 5 nm is made of a lipid with the lowest transition temperature among the lipids.

10. The method for producing a proteoliposome according to claim 2 or 4, wherein the region of a lipid bilayer membrane with different membrane thickness includes: a portion of a lipid bilayer with a layer thickness of approximately 7 nm; and a portion of a lipid bilayer with a layer thickness of approximately 5 nm, the portion of a lipid bilayer with a layer thickness of approximately 7 nm is made of a lipid with the highest transition temperature among the lipids, and the portion of a lipid bilayer with a layer thickness of approximately 5 nm is made of a lipid with the lowest transition temperature among the lipids.

* * * * *